(12) United States Patent
Pillai et al.

(10) Patent No.: US 6,358,517 B1
(45) Date of Patent: Mar. 19, 2002

(54) COSMETIC COMPOSITIONS CONTAINING RESVERATROL AND RETINOIDS

(75) Inventors: Sreekumar Pillai, Wayne; Manisha Narayan Mahajan, Westwood; Stewart Paton Granger, Paramus; David Joseph Pocalyko, Wayne; Marieann Barratt, Oak Ridge, all of NJ (US)

(73) Assignee: Unilever Home & Personal Care USA, division of Conopco, Greenwich, CT (US)

( * ) Notice: Subject to any disclaimer, the term of this patent is extended or adjusted under 35 U.S.C. 154(b) by 0 days.

(21) Appl. No.: 09/663,764

(22) Filed: Sep. 18, 2000

Related U.S. Application Data

(60) Provisional application No. 60/160,970, filed on Oct. 22, 1999.

(51) Int. Cl.⁷ .............................. A61K 7/00; A61K 7/40; A61K 7/48
(52) U.S. Cl. ....................... 424/401; 424/448; 424/616; 424/58
(58) Field of Search ................................ 424/616, 401, 424/448, 58

(56) References Cited

U.S. PATENT DOCUMENTS

| | | | |
|---|---|---|---|
| 5,171,577 A | 12/1992 | Griat et al. ................. | 424/450 |
| 5,391,724 A | 2/1995 | Kindl et al. ................ | 536/23.2 |
| 5,439,672 A | 8/1995 | Zabotto et al. .............. | 424/59 |
| 5,605,894 A * | 2/1997 | Blank et al. ................ | 424/59 |
| 5,683,683 A | 11/1997 | Scafidi ....................... | 424/70 |
| 5,834,513 A | 11/1998 | Ptchelintsev et al. ....... | 514/561 |
| 5,847,003 A | 12/1998 | Ptchelintsev et al. ....... | 514/532 |
| 5,935,596 A * | 8/1999 | Crotty et al. ............... | 424/448 |
| 6,071,541 A * | 6/2000 | Murad ........................ | 424/616 |
| 6,124,364 A | 9/2000 | Breton et al. ............... | 514/733 |
| 6,147,121 A | 11/2000 | Breton et al. ............... | 514/726 |

FOREIGN PATENT DOCUMENTS

| | | |
|---|---|---|
| FR | 2 777 183 | 10/1999 |
| FR | 2 777 186 | 10/1999 |
| WO | 99/04747 | 2/1999 |

OTHER PUBLICATIONS

PCT International Search Report in a PCT application PCT/EP 00/09515.
Derwent Abstract of JP 6336421, dated Dec. 6, 1994.
Jang et al., Cancer Chemopreventive Activity of Resveratrol, a Natural Product Derived from Grapes, Science 275: 218–220, 1997.
Creidi et al., Effect Of A Conjugated Oestrogen Cream Premarin® On Aging Facial Skin, Maturitas, 19 p. 211–23, 1994.
Knight et al., Phytoestrogens—A Short Review, Maturitas, 22: 167–175, 1995.
Gehm et al., Resveratrol, a polyphenolic compound found in grapes and wine, is an agonist for the estrogen receptor, Proc. Natl. Acad. Sci. USA, vol. 94, pp 14138–14143, Dec. 1997.

\* cited by examiner

*Primary Examiner*—Diana Dudash
*Assistant Examiner*—Mina Haghighatian
(74) *Attorney, Agent, or Firm*—Ellen Plotkin

(57) ABSTRACT

Cosmetic skin care compositions containing resveratrol in combination with selected retinoids.

3 Claims, No Drawings

COSMETIC COMPOSITIONS CONTAINING RESVERATROL AND RETINOIDS

This application claims the benefit of U.S. provisional application No. 60/160,970 filed Oct. 22, 1999.

FIELD OF THE INVENTION

Cosmetic compositions containing resveratrol in combination with retinoids and methods of conditioning skin by applying such compositions to the skin.

BACKGROUND OF THE INVENTION

Estrogens and synthetic compounds which act like estrogens are known to increase the thickness of the dermal layer and reduce wrinkle formation in the aging skin. Changes in the skin such as skin dryness, loss of skin elasticity and plumpness occurring after menopause are attributed to the lack of estrogen production. Estrogen therapy prevents or slows down many of the changes associated with aging skin (Creidi et al., Effect of a conjugated oestrogen cream (Premarin®) on aging facial skin, Maturitas, 19, p.211–23, 1994). Natural estrogen, estradiol, has the following structure:

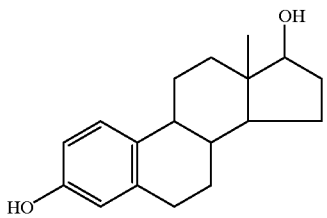

Retinol (vitamin A) is an endogenous compound which occurs naturally in the human body and is essential for normal epithelial cell differentiation. Natural and synthetic vitamin A derivatives have been used extensively in the treatment of a variety of skin disorders and as skin repair and renewal agents. Retinoic acid has been used to treat a variety of skin conditions such as acne, wrinkles, psoriasis, age spots and skin discoloration.

Estradiol induces the expression of retinoid receptors in 2 different cell types. In mouse cervical epithelial cells estradiol stimulates the expression of retinoid X receptors and retinoic acid receptors (Exp Cell Res., 226: 273, 1996). In breast cancer cells estradiol induces the expression of a subtype of retinoic acid receptor gene expression (Mol. Endocrinol. 12: 882, 1998). Human skin expresses large amounts of the same types of retinoic acid receptors and retinoid X receptors (Voorhees et al, skin pharmacol., 6:70, 1993). However, unlike breast or cervix, skin is not a target organ for estrogen action.

Ptchelintsev et al. (U.S. Pat. Nos. 5,847,003 and 5,834, 513) disclose compositions containing oxaacids and related compounds and which may further include numerous optional ingredients, among which are mentioned estradiol, retinoids and bioflavonoids.

The consumer demand for products containing plant extracts or ingredients derived from plants has been growing in recent years. Such products are perceived by consumers as pure and mild and superior to chemically synthesized products.

Phytoestrogens are natural compounds which have estrogen-like activity and which are found in plants. Some bioflavonoids, such as genistein and daidzein, are known phytoestrogens. WO 99/04747 (Unilever) teaches that resveratrol, a compound found in a variety of plants, is a phytoestrogen and discloses cosmetic compositions containing resveratrol. One of the disclosed compositions also includes retinyl palmitate.

The present invention is based in part on the discovery that not all phytoestrogens and not all retinoids exhibit synergy when combined. The combination of resveratrol with selected retinoids, however, synergistically enhanced the beneficial effects of retinoids on skin.

The art discussed above does not describe the presently claimed combinations of resveratrol and retinoids for skin care cosmetic use.

SUMMARY OF THE INVENTION

The present invention includes a cosmetic skin care composition comprising resveratrol in an amount of from 0.00001 to 10 wt. %, a retinoid selected from the group consisting of retinoic acid, retinol, retinyl acetate and retinyl linoleate, and a cosmetically acceptable vehicle.

The present invention also includes a method of improving or preventing the condition of wrinkled, lined, dry, flaky, aged or photodamaged skin and improving skin thickness, elasticity, flexibility, radiance, glow and plumpness, which method includes applying to the skin the inventive composition. Compositions of the invention are intended for topical application to mammalian skin which is already dry, flaky, lined, wrinkled, aged, photodamaged, or the inventive compositions may be applied prophylactically to reduce the deteriorative changes.

DETAILED DESCRIPTION OF THE INVENTION

Except in the examples, or where otherwise explicitly indicated, all numbers in this description indicating amounts of material or conditions of reaction, physical properties of materials and/or use are to be understood as modified by the word "about." All amounts are by weight of the composition, unless otherwise specified.

Resveratrol (also known as 5-parahydroxystyryl resorcinol, or 3,4'5-stilbenetriol) is an essential ingredient of the inventive composition. Resveratrol has the following structure:

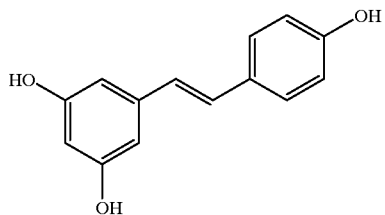

Pure resveratrol may be obtained commercially from Sigma, and in crude form from other cosmetic suppliers such as DNP International, Pharma Science or Madis Botanicals.

In general, the amount of resveratrol in the inventive compositions is in the range of from 0.00001 to 10% by weight composition. Preferably in order to lower cost and maximize the effect the amount of resveratrol is in the range of from 0.001% to 5% and most preferably is in the range of from 0.1% to 5%.

The inventive compositions further comprise a retinoid selected from the group consisting of retinoic acid, retinol, retinyl acetate, and retinyl linoleate. It has been found that these retinoids, but not retinyl palmitate, act synergistically in combination with resveratrol.

Most preferred retinoid is selected from retinol, retinyl acetate and retinyl linoleate, because of its proven cosmetic efficacy.

The retinoid is generally employed in the inventive compositions in an amount of from 0.001 to 10%, preferably from 0.01 to 1, most preferably from 0.01 to 0.5% by weight of the compositions.

The composition according to the invention also comprises a cosmetically acceptable vehicle to act as a diluant, dispersant or carrier for resveratrol and the reinoid in the composition, so as to facilitate their distribution when the composition is applied to the skin.

Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 $mm^2/s$ (centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

The inventive compositions preferably include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical cosmetic application to human skin, especially as an agent for conditioning, moisturizing and smoothening the skin, and preventing or reducing the appearance of lined, wrinkled or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Product Form and Packaging

The topical skin treatment composition of the invention can be formulated as a lotion, a cream or a gel. The composition can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507, incorporated by reference herein. The invention accordingly also provides a closed container containing a cosmetically acceptable composition as herein defined.

The following specific examples further illustrate the invention, but the invention is not limited thereto. In all examples, resveratrol was obtained from Sigma. Retinoids were obtained from Sigma. Student t-test was used to calculate all p-values.

The following Methods were Employed:

Leo Cell Culture Method

Human adult fibroblasts obtained from sun-protected inner arm of the 25–30 year female volunteer were used. Cells were grown in 1:1 DMEM/Hams F12 media containing 10% FBS, maintained at 37° C. in a 5% CO2 atmosphere under normal atmospheric oxygen tension. Third passage adult fibroblasts were grown in DMEM media with 10% FBS in 12-well plates at a seeding density of 40,000 cells/ml/well. The cells at 80% confluence were rinsed in serum free and phenol red free (PRF) DMEM media twice. Cells were pretreated with resveratrol for 4 hours was conducted and then dosed with retinoids and incubated for a further 48 hours. After the incubation, the wells were washed twice with 1×PBS and the cell monolayer was harvested in 100 µl cell lysis buffer (contained 1×PBS, 1% TritonX, 0.5% sodium deoxycholate, 0.1% SDS containing protease inhibitor (10 mg/ml PMSF in isopropanol, 10 µl/ml). The suspension was spun at 14000 rpm for 10 minutes, the supernatant collected and an aliquot of this supernatant was used for protein quantification. Protein concentration was determined using Pierce protein kit. The remainder of 1 00ul supernatant (cell lysate) was denatured in a mixture of 40 µl sample buffer (NOVEX) and 0.5% Beta mercaptoethanol (BME) and by boiling the sample for 5 minutes.

Pig Skin Organ Culture Method 7 mm pig skin biopsies were taken, plated in serum free DMEM, and incubated for 2 days. The media was then switched to phenol-red free media. The biopsies were topically treated with resveratrol for 24 hrs in 5 µl ethanol per biopsy. After 24 hours, retinoids were topically applied to the biopsies. The treated biopsies were incubated for 4 days thereafter. After treatment phase, the biopsies were rinsed in 1×phosphate-buffer twice and then frozen at −20° C. for future use. The epidermis and dermis was separated by freezing and scraping off the epidermis. The epidermis was collected and homogenized in lysis buffer (contains 1×PBS, 1% TritonX, 0.5% sodium deoxycholate, 0.1% SDS containing protease inhibitor (10 mg/ml PMSF in isopropanol at 10 µl/ml, Aprotinin 30 µl/ml and 100 mM sodium orthovanadate at 10 µl/ml). This homogenate was then spun at 14000 rpm and the supernatant was collected for determining protein (aliquot of the supernatant for protein determination).

Detection of Cellular Retinoic Acid Binding Protein 2 (CRABP-2) in Fibroblasts and Pig Skin Biopsies Within the cells, retinol and retinoic acid are bound to specific cellular binding proteins. Two of the major proteins are CRABP-1 and CRABP-2 (Roos et al., Pharmacological reviews: 50, 315–333, 1998). These proteins regulate the intracellular concentration of retinoids by acting as either storage or shuttle proteins in retinoid metabolism. The levels of CRABP protein are regulated by the amount of retinoic acid within the cells. Higher cellular levels of retinoids increase the expression of CRABP-2. Therefore, the amount of this protein in the cells, is a measure of the retinoid activity of the cells. Skin cells contain high levels of CRABP-2 both in the epidermis and the dermis. CRABP-2 response to retinoid administration in fibroblasts in vitro is used as a reproducible measure of retinoid bioactivity that predict human skin responses (Elder et al., J. Invest. Dermatol., 106: 517–521, 1996). Increase in CRABP-2 is also associated with increased epidermal differentiation, and dermal retinoid action. Therefore, in these studies we used CRABP-2 expression of fibroblasts and pig skin epidermis as a measure of retinoid activity leading to increased epidermal differentiation (skin conditioning and dry skin benefit) and dermal collagen and extracellular matrix synthesis (antiaging, anti wrinkling benefits).

To measure the levels of CRABP-2 in the fibroblast and pig skin extracts prepared as described above, the cell supernatant was re-suspended in 4×sample buffer and 10% BME, boiled for 5 minutes and used for western blotting. Equal amounts of protein were loaded onto 16% Tris-glycine gels for CRABP-2 protein analysis by SDS-PAGE and Western Immuno-blotting. The gels were transferred to PVDF membranes and Western Blotting was carried out using monoclonal antibodies to CRABP-2 according to standard procedures. The CRABP-2 protein band was visualized in the Western Blots using the chemiluminescence system obtained from Boehringer Mannheim (Indianapolis, Ind.). The bands in the film were quantified by densitometric scanning, the data from triplicate samples were calculated as % of control and expressed in the following tables as % increase over control (with control as 100%) +/− standard deviation.

EXAMPLE 1

The effect on skin of using the combination of resveratrol with retinol or retinoic acid was tested using pig skin organ culture method. The results that were obtained are summarized in Table 1.

Control in the first experiment was 0.0763+/−0.0259 and in the second experiment 0.11+/−1.01 OD.

TABLE 1

|  | Alone | p-value (vs. control) | Retinoid + resveratrol | p-value (vs. Retinoid) | Synergy at p < 0.05 |
| --- | --- | --- | --- | --- | --- |
| Experiment 1 |  |  |  |  |  |
| Control | 100 +/− 33.9 | — |  |  |  |
| 1 µM retinoic acid | 3207 +/− 716 | 0.003 |  |  |  |
| 50 µM Resveratrol | 143 +/− 64 | 0.448 | 930 +/− 80 | 0.027 | Yes |

TABLE 1-continued

|  | Alone | p-value (vs. control) | Retinoid + resveratrol | p-value (vs. Retinoid) | Synergy at $p < 0.05$ |
|---|---|---|---|---|---|
| Experiment 2 | | | | | |
| Control | 100 +/- 9 | — | | | |
| 5 μM retinol | 345 +/- 89 | 0.058 | | | |
| 20 μM Resveratrol | 242 +/- 189 | 0.470 | 1581 +/-81 | 0.003 | Yes |

It can be seen from the results in Table 1 that resveratrol alone showed only minimal, insignificant effects on CRABP-2 expression. Retinol and retinoic acid showed significantly higher stimulation of CRABP-2 expression. When the pig skin epidermis was pretreated with resveratrol, resveratrol synergistically enhanced retinol and retinoic acid activity.

EXAMPLE 2

The effect on skin of using resveratrol with retinoids, including retinyl esters was investigated in human skin fibroblasts. The results that were obtained in 2 separate experiments are summarized in Tables 2A and 2B, respectively.

TABLE 2A

| | CRAB-2 production | % of Control | p value vs. Control | p value vs. retiniods | p value vs. resveratrol | Synergy at p? |
|---|---|---|---|---|---|---|
| Control | 1.546 +/- 0.44 | 100 +/- 28 | 1 | | | |
| 10 nM Retinoic acid | 2.566 +/- 0.19 | 165 +/- 12 | 0.02 | 1 | | |
| 1 nM Retinoic acid | 2.056 +/- 0.50 | 132 +/- 32 | 0.25 | 1 | | |
| 100 nM Retinyl Linoleate | 0.88 +/- 0.23 | 57 +/- 14 | 0.08 | 1 | | |
| 100 nM Retinyl Palmitate | 0.376 +/- 0.11 | 25 +/- 7 | 0.01 | 1 | | |
| 100 nM Retinyl Acetate | 0.876 +/- 0.20 | 56 +/- 13 | 0.07 | 1 | | |
| 10 μM Resveratrol | 0.416 +/- 0.12 | 27 +/- 8 | 0.013 | | 1 | |
| 10 μM Resveratrol + 10 nM Retinoic acid | 4.926 +/- 0.29 | 318 +/- 19 | 0.00039 | 0.000318 | 1.70E-05 | Yes |
| 10 μM Resveratrol + 1 nM Retinoic acid | 3.54 +/- 0.60 | 229 +/- 38 | 0.0098 | 0.03 | 0.000916 | Yes |
| 10 μM Resveratrol + 100 nM Retinyl linoleate | 1.911 +/- 0.022 | 124 +/- 14 | 0.23 | 0.016 | 0.002253 | Yes |
| 10 μM Resveratrol + 100 nM Retinyl palmitate | 0.576 +/-0.25 | 37 +/- 16 | 0.03 | 0.288 | 0.3888 | No |
| 10 μM Resveratrol + 100 nM Retinyl acetate | 0.75 +/- 0.28 | 49 +/- 18 | 0.05 | 0.56 | 0.1416 | No |

TABLE 2B

| | CRABP-2 production | % as Control | p value vs. control | p value vs. retinoids | p Value vs. active | Synergy at p? |
|---|---|---|---|---|---|---|
| Control | 0.57 +/- 0.18 | 100 +/- 31 | 1 | | | |
| 10 μM Retinoic acid | 3.27 +/- 0.34 | 574 +/- 60 | 0.000275 | 1 | | |
| 1 uM Retinol | 1.54 +/- 0.41 | 270 +/- 73 | 0.0208 | 1 | | |
| 1 μM Retinyl Palmitate | 2.87 +/- 1.48 | 503 +/- 260 | 0.062 | 1 | | |
| 1 μM Retinyl Linoleate | 0.64 +/- 0.4.3 | 112 +/- 75 | 0.8 | 1 | | |
| 1 μM Retinyl Acetate | 1.01 +/- 0.58 | 178 +/- 102 | 0.27 | 1 | | |
| 10 μM Resveratrol | 0.185 +/- 0.007 | 32 +/- 1 | 0.06 | | 1 | |
| 10 μM Resveratrol + 10 nM Retinoic acid | 4.78 +/- 0.02 | 839 +/- 4 | 7.10E-05 | 0.0098 | 1.18E-05 | Yes |
| 10 μM Resveratrol + 1 uM Retinol | 1.75 +/- 0.55 | 307 +/- 96 | 0.034 | 0.611 | 0.05 | No |
| 10 μM Resveratrol + 1 μM Retinyl Palmitate | 0.51 +/- 0.4 | 90 +/- 71 | 0.845 | 0.067 | 0.35 | No |
| 10 μM Resveratrol + 1 μM Retinyl Linoleate | 3.66 +/- 0.99 | 641 +/- 174 | 0.006 | 0.0085 | 0.01 | Yes |
| 10 μM Resveratrol + 1 μM Retinyl Acetate | 3.78 +/- 0.77 | 664 +/- 135 | 0.002 | 0.0077 | 0.0082 | Yes |

It can be seen from the results in Tables 2A and 2B that resveratrol in combination with retinoids, synergistically stimulated CRABP-2 expression in skin fibroblasts, except when resveratrol was combined with retinyl palmitate (which was not effective in either of the experiments. Retinol was effective in the second experiment where it was tested (retinol was not tested in the first experiment—Table 2A). Low levels of retinyl acetate (100 nm) either alone or in combination with resveratrol, were ineffective. However, at higher levels (Table 2B) retinyl acetate stimulated CRABP-2 expression in the presence of reveratrol.

COMPARATIVE EXAMPLE 3

This example investigated the effect on skin of combination of soy extract (which is a known phytoestrogen) and retinoids.

In this example, soy powder obtained from ADM (Nova Soy) was dissolved in ethanol as a 1 mg/ml solution, heated to 70° C. for half hour and filtered. The alcoholic extract was used to test in the assays. The results that were obtained are summarized in Table 3.

TABLE 3

| | CRABP-2 production | % as Control | p value vs Control | p value vs retiniods | Synergy at p? |
|---|---|---|---|---|---|
| Control | 0.450 +/- 0.18 | 100 +/- 42 | 1 | | |
| 10 nM Retinoic acid | 1.201 +/- 0.36 | 266 +/- 80 | 0.033 | 1 | |
| 100 nM Retinol | 1.387 +/- 0.49 | 308 +/- 108 | 0.036 | 1 | |
| 100 nM Retinyl Linoleate | 1.141 +/- 0.57 | 253 +/- 127 | 0.118 | 1 | |
| 100 nM Retinyl Palmitate | 1.143 +/- 0.45 | 254 +/- 101 | 0.072 | 1 | |
| 100 nM Retinyl Acetate | 0.561 +/- 0.19 | 124 +/- 42 | 0.51 | 1 | |
| 0.0001% Soy | 1.808 +/- 0.746 | 401 +/- 165 | 0.047 | | |
| 0.0001% Soy + 10 nM Retinoic acid | 2.206 +/- 0.73 | 490 +/- 162 | | 0.099 | No |
| 0.0001% Soy + 100 nM Retinol | 1.553 +/- 0.98 | 345 +/- 218 | | 0.805 | No |

TABLE 3-continued

| | CRABP-2 production | % as Control | p value vs Control | p value vs retiniods | Synergy at p? |
|---|---|---|---|---|---|
| 0.0001% Soy + 100 nM Retinyl Linoleate | 1.637 +/− 0.45 | 363 +/− 100 | | 0.304 | No |
| 0.0001% Soy + 100 nM Retinyl Palmitate | 1.143 +/− 0.24 | 254 +/− 55 | | 0.123 | No |
| 0.0001% Soy + 100 nM Retinyl Acetate | 0.782 +/− 0.38 | 173 +/− 84 | | 0.419 | No |

As seen from Table 3, soy extract alone stimulated CRABP-2 expression of fibroblasts by 400% of control (to the same levels as retinoids). The different retinoids stimulated CRABP-2 expression from 200–400% of control. However, when combined together, soy did not synergize with the different retinoids. The combination was in most cases even less active than either agent alone. Thus, soy extract, although it is a phytoestrogen, did not exhibit synergy with retinoids in the expression of CRABP-2 in fibroblasts.

Examples 4–9 illustrate skin care compositions according to the present invention. The compositions can be processed in conventional manner. They are suitable for cosmetic use. In particular, the compositions are suitable for application to wrinkled, lined, rough, dry, flaky, aged and/or UV-damaged skin to improve the appearance and the feel thereof as well as for application to healthy skin to prevent or retard deterioration thereof.

EXAMPLE 4

This example illustrates a high internal phase water-in-oil emulsion incorporating the inventive composition.

| | % w/w |
|---|---|
| Resveratrol | 0.5 |
| Retinol | 0.5 |
| 1,3-dimethyl-2-imidazolidinone | 0.2 |
| Brij 92* | 5 |
| Bentone 38 | 0.5 |
| $MgSO_4 7H_2O$ | 0.3 |
| Butylated hydroxy toluene | 0.01 |
| Perfume | qs |
| Water | to 100 |

*Brij 92 is polyoxyethylene (2) oleyl ether

EXAMPLE 5

This example illustrates an oil-in-water cream incorporating the inventive composition.

| | % w/w |
|---|---|
| Resveratrol | 2 |
| Retinyl linoleate | 0.5 |
| Glycolic Acid | 8 |
| Mineral oil | 4 |
| 1,3-dimethyl-2-imidazolidinone | 1 |

-continued

| | % w/w |
|---|---|
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 6

This example illustrates an alcoholic lotion incorporating the composition according to the invention.

| | % w/w |
|---|---|
| Resveratrol | 5 |
| Retinyl acetate | 0.5 |
| Retinyl Linoleate | 1.0 |
| 1,3-dimethyl-2-imidazolidinone | 0.1 |
| Ethanol | 40 |
| Perfume | qs |
| Butylated hydroxy toluene | 0.01 |
| Water | to 100 |

EXAMPLE 7

This example illustrates another alcoholic lotion containing the inventive composition.

| | % w/w |
|---|---|
| Resveratrol | 5 |
| Retinol | 1.0 |
| 1,3-dimethyl-2-imidazolidinone | 0.01 |
| Ethanol | 40 |
| Antioxidant | 0.1 |
| Perfume | qs |
| Water | to 100 |

EXAMPLE 8

This example illustrates a suncare cream incorporating the composition of the invention:

|  | % w/w |
|---|---|
| Resveratrol | 2 |
| Retinyl Linoleate | 2.0 |
| 1,3-dimethyl-2-imidazolidinone | 0.2 |
| Silicone oil 200 cts | 7.5 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 9

This example illustrates a non-aqueous skin care composition incorporating the inventive combination.

|  | % w/w |
|---|---|
| Resveratrol | 5 |
| Retinol | 1.0 |
| 1,3-dimethyl-2-imidazolidinone | 1 |
| Retinyl Linoleate | 1.0 |
| Silicone gum SE-30[1] | 10 |
| Silicone fluid 345[2] | 20 |
| Silicone fluid 344[3] | 50.26 |
| Squalene | 10 |
| Linoleic acid | 0.01 |
| Cholesterol | 0.03 |
| 2-hydroxy-n-octanoic acid | 0.7 |
| Vitamin E linoleate | 0.5 |
| Herbal oil | 0.5 |
| Ethanol | 2 |

[1]A dimethyl silicone polymer having a molecular weight of at least 50,000 and a viscosity of at least 10,000 centistokes at 25° C., available from GEC
[2]Dimethyl siloxane cyclic pentamer, available from Dow Corning Corp.
[3]Dimethyl siloxane tetramer, available from Dow Corning Corp.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin care composition comprising:
   (i) resveratrol in an amount of from 0.00001 to 10 wt. %;
   (ii) a retinoid selected from the group consisting of retinoic acid, retinol, and retinyl acetate; and
   (iii) a cosmetically acceptable vehicle;
   wherein said retinoid is present in an amount of about 0.001 to about 10 wt. %.

2. A cosmetic method of improving the appearance of wrinkled, lined, dry, flaky, aged or photodamaged skin and improving skin thickness, elasticity, flexibility and plumpness, the method comprising applying to the skin the composition of claim 1.

3. A cosmetic method of increasing the level of cellular retinoic acid binding protein in the skin, the method comprising applying to the skin the composition of claim 1.

* * * * *